(12) United States Patent
Scheunemann et al.

(10) Patent No.: US 10,383,812 B2
(45) Date of Patent: Aug. 20, 2019

(54) HAIR TREATMENT AGENTS

(71) Applicant: Henkel AG & Co. KGaA, Duesseldorf (DE)

(72) Inventors: Volker Scheunemann, Lueneburg (DE); Erik Schulze zur Wiesche, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 32 days.

(21) Appl. No.: 15/365,718

(22) Filed: Nov. 30, 2016

(65) Prior Publication Data

US 2017/0151166 A1 Jun. 1, 2017

(30) Foreign Application Priority Data

Dec. 1, 2015 (DE) .................. 10 2015 223 843

(51) Int. Cl.
| | | |
|---|---|---|
| *A61Q 5/12* | (2006.01) | |
| *A61K 8/898* | (2006.01) | |
| *A61K 8/34* | (2006.01) | |
| *A61K 8/41* | (2006.01) | |
| *A61K 8/64* | (2006.01) | |
| *A61K 8/73* | (2006.01) | |
| *A61Q 5/00* | (2006.01) | |
| *A61Q 5/02* | (2006.01) | |

(52) U.S. Cl.
CPC .............. *A61K 8/898* (2013.01); *A61K 8/34* (2013.01); *A61K 8/342* (2013.01); *A61K 8/347* (2013.01); *A61K 8/416* (2013.01); *A61K 8/64* (2013.01); *A61K 8/731* (2013.01); *A61Q 5/004* (2013.01); *A61Q 5/02* (2013.01); *A61Q 5/12* (2013.01); *A61K 2800/5426* (2013.01); *A61K 2800/594* (2013.01); *A61K 2800/596* (2013.01)

(58) Field of Classification Search
None
See application file for complete search history.

(56) References Cited

U.S. PATENT DOCUMENTS

| | | | | |
|---|---|---|---|---|
| 4,867,971 | A * | 9/1989 | Ryan .................... | A61K 8/4946 514/399 |
| 2003/0082129 | A1* | 5/2003 | Buckingham .......... | A61K 8/046 424/70.12 |
| 2011/0274640 | A1* | 11/2011 | Schulze Zur Wiesche ................. | A61K 8/64 424/70.13 |
| 2014/0069452 | A1* | 3/2014 | Krueger ................ | A61K 8/416 132/202 |

FOREIGN PATENT DOCUMENTS

EP 2438900 A1 4/2012

* cited by examiner

*Primary Examiner* — Jyothsna A Venkat
(74) *Attorney, Agent, or Firm* — Fabian VanCott; Steven Nichols

(57) ABSTRACT

Hair treatment agents including: at least one fatty alcohol, at least one cationic surfactant, at least one aminofunctional silicone, o-cymen-5-ol, and phenoxyethanol.

13 Claims, No Drawings
Specification includes a Sequence Listing.

HAIR TREATMENT AGENTS

BACKGROUND

The present invention relates to hair treatment agents. In particular, to shampoos and conditioners having active ingredients for hair care.

The importance of hair care products with the longer performance has grown. This is due in part to increased stress on hair, for example, from dyeing, permanent waves, cleaning of hair with shampoos, and due to environmental pollution. Such hair care products have an influence on the natural structure and properties of hair. For example, the wet and dry combability of hair, the hold and body of hair, and/or protection from increased split ends may be impacted by use of appropriate hair care products.

It has been customary to subject hair to special after-treatments in which the hair is treated with special active ingredients, for example, quaternary ammonium salts or special polymers. This is usually in the form of a rinse. These treatments may result in improved combability, hold, and body of hair while reducing the amount of split ends, depending on the formulation.

Multifunctional cosmetic products are also known in the prior art. In particular, this includes "two-in-one" shampoos, which clean and condition the hair. Such products are appreciated by consumers because the product eliminates the need for at least one procedural step, e.g., conditioning with a traditional hair conditioner.

DETAILED DESCRIPTION

This document incorporates by reference, in its entirety, the file "PT033609 SEQUENCE LISTING.txt" created Apr. 1, 2019 and having a size of 1229 bytes. Products for changing the natural hair color also play a prominent role in hair cosmetics. A distinction is made between permanent, semi-permanent, or temporary dyeing systems, these being based on chemical and/or natural dyes. The hair colors produced artificially by permanent, semi-permanent or temporary dyes, however, have the disadvantage that they can change undesirably, for example during or after cleaning of the hair.

The term "undesirable change" is understood to mean the fading or bleeding and also the loss of the color brilliance of the coloring of the hair attained by the respective dyeing. Ambient influences and/or the effects of the sun can intensify these changes further.

The use of bivalent metal salts in hair dyes to improve the durability and therefore fastness of the coloration is known from EP 2438900 A1, which is incorporate by reference herein.

There is still a need to provide active substances or active substance combinations for hair treatment agents having good nourishing properties which in addition increase the adhesion of dyes to the hair fibers and thus preserve the fastness of the artificially produced hair color, and also to further develop hair treatment agents in this respect.

It has now been found that a combination of certain ingredients has a particularly positive effect on dyed hair and the hair follicle treated with said ingredients.

A first subject of the present invention is constituted by hair treatment agents which includes: at least one fatty alcohol, at least one cationic surfactant, at least one amino-functional silicone, o-Cymen-5-ol, and phenoxyethanol.

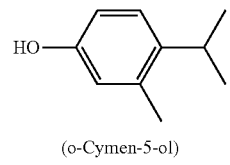

(o-Cymen-5-ol)

Hair treatment agents in the sense of the present invention include, for example: hair shampoos, hair conditioners, conditioning shampoos, hairsprays, hair rinse-out treatments, hair deep treatments, hair masks, hair tonics, permanent wave fixing solutions, hair-coloring shampoos, hair dyes, hair fixers, hair setting agents, hairstyling preparations, blow-dry lotions, foam fixers, hair gels, hair waxes, and/or combinations thereof. As men often avoid the application of a number of different agents and/or a number of application steps, agents that can be readily applied by men are preferred. Preferred agents include: shampoos, conditioning agents, and/or hair tonics.

The hair treatment agents include at least one fatty alcohol. Fatty alcohols are aliphatic, long-chain, monovalent primary alcohols having hydrocarbon groups comprising 6 to 30, preferably 6 to 22 carbon atoms. The hydrocarbon groups can be saturated or mono- or polyunsaturated. Preferred fatty alcohols that can be used with preference within the scope of the present invention are selected from 1-hexanol, 1-heptanol, 1-octanol, 1-decanol, 1-dodecanol (lauryl alcohol), 1-tetradecanol (myristyl alcohol), 1-hexadecanol (cetyl alcohol), 1-heptadecanol (margaryl alcohol), 1-octadecanol (stearyl alcohol), 1-eisosanol (arachidyl alcohol), 1-docosanol (behenyl alcohol), 1-tetracosanol (lignoceryl alcohol), 1-hexacosanol (ceryl alcohol), 1-octacosanol (montanyl alcohol), 1-triacontanol (melissyl alcohol), cis-9-hexadecen-1-ol (palmitoleyl alcohol), cis-9-octadecen-1-ol (oleyl alcohol), trans-9-octadecen-1-ol (elaidyl alcohol), cis-11-octadecen-1-ol, 6,9,12-octadecatrien-1-ol (γ-linolenyl alcohol) and mixtures thereof.

Particularly preferred hair treatment agents are characterized in that they include, in relation to the weight of the agent, 0.1 to 20% by weight, preferably 0.5 to 15% by weight, more preferably 1 to 10% by weight, and in particular 2 to 8% by weight of fatty alcohol(s) of formula (II)

$$H_3C-(CH_2)_k-CH_2-OH \quad (II)$$

wherein k stands is an integer from 4 to 28 inclusive, preferably from 6 to 24, more preferably from 8 to 22, and in particular 10, 12, 14, 16, 18 or 20.

Particularly preferred hair treatment agents according to the invention include, in relation to the weight of the agent, 0.1 to 20% by weight, preferably 0.5 to 15% by weight, more preferably 1 to 10% by weight, and in particular 2 to 8% by weight of alcohol(s) from the group 1-dodecanol (lauryl alcohol), 1-hexadecanol (cetyl alcohol), 1-octadecanol (stearyl alcohol), 1-docosanol (behenyl alcohol), wherein the amounts relate to the total amount of the specified fatty alcohols in the composition.

Very particularly preferred hair treatment agents according to the invention include, in relation to the weight of the agent, 0.1 to 20% by weight, preferably 0.5 to 15% by weight, more preferably 1 to 10% by weight, and in particular 2 to 8% by weight of alcohol(s) from the group 1-hexadecanol (cetyl alcohol), 1-octadecanol (stearyl alcohol), wherein the amounts relate to the total amount of the specified fatty alcohols in the composition.

The hair treatment agents include at least one cationic surfactant.

The cationic surfactant(s) is/are preferably selected from the group of quaternary ammonium compounds and/or amidoamines, wherein preferred cationic surfactant(s) is/are selected from: alkyltrimethylammonium chlorides having preferably 10 to 18 carbon atoms in the alkyl group; dalkyldimethylammonium chlorides having preferably 10 to 18 carbon atoms in the alkyl group; trialkylmethylammonium chlorides having preferably 10 to 18 carbon atoms in the alkyl group; cetyl trimethyl ammonium chloride; stearyl trimethyl ammonium chloride; behenyl trimethyl ammonium chloride; distearyl dimethyl ammonium chloride; lauryl dimethyl ammonium chloride; lauryl dimethyl benzyl ammonium chloride; tricetyl methyl ammonium chloride; quaternium-27; quaternium-83; and/or mixtures thereof.

Hair treatment agents that are preferred in accordance with the invention include, in relation to the weight of the agent, 0.05 to 20% by weight, preferably 0.1 to 10% by weight, more preferably 0.25 to 8% by weight, and in particular 0.5 to 7% by weight of cationic surfactant(s).

Particularly preferred cationic surfactants are selected from compounds of the following formula (III)

(III)

in which no more than three groups R1 to R4, independently of one another, stand for a saturated or unsaturated, branched or unbranched alkyl group having 1 to 4 carbon atoms, at least one group R1 to R4 stands for a saturated or unsaturated, branched or unbranched alkyl chain having 8 to 30 carbon atoms, and A is a physiologically acceptable organic or inorganic anion.

In preferred compounds according to formula (III): two or more groups R1 to R4 stand for a methyl group or an ethyl group; one or two group(s) R1 to R4 stands/stand for a saturated or unsaturated, branched or unbranched alkyl chain having 14 to 26 carbon atoms; and A stands for a halide ion, a sulfate ion of general formula $RSO_3-$, in which R means saturated or unsaturated alkyl groups having 1 to 4 carbon atoms, or stands for an anionic group of an organic acid such as maleic acid, fumaric acid, oxalic acid, tartaric acid, citric acid, lactic acid, or acetic acid.

More preferred are compounds according to formula (III), in which: three groups R1 to R4 are methyl groups; one group R1 to R4 is a cetyl group, palmityl group, stearyl group, arachidyl group, or a behenyl group; and A is a chloride or a methosulfate ion.

The at least one compound according to formula (III) is particularly preferably selected from cetyl trimethyl ammonium chloride, cetyl trimethyl ammonium methosulfate, behenyl trimethyl ammonium chloride and/or behenyl trimethyl ammonium methosulfate. These compounds can be used in the agent according to the invention individually or in combination, wherein the total amount of compounds of formula (III) in the agent is preferably at most 10% by weight, and wherein the specified amount relates to the total weight of the agent according to the invention.

An agent according to the invention particularly preferably includes behenyl trimethyl ammonium chloride as cationic surfactant. Here, preferred hair treatment agents according to the invention are those that, in relation to the weight of the agent, include 0.05 to 20% by weight, preferably 0.1 to 10% by weight, more preferably 0.25 to 8% by weight, and in particular 0.5 to 7% by weight of behenyl trimethyl ammonium chloride.

The hair treatment agents can also include at least one esterquat as cationic surfactant. The term "esterquats" in the sense of the present invention is understood preferably to mean compounds of the following formula (IV)

(IV)

in which: the groups R5, R6 and R7, each independently of one another, can be the same or different and have the following meaning: a saturated or unsaturated, branched or unbranched alkyl group having 1 to 4 carbon atoms which can include at least one hydroxyl group; a saturated or unsaturated, branched or unbranched or a cyclic saturated or unsaturated alkyl group having 6 to 30 carbon atoms which can include at least one hydroxyl group; an aryl or alkylaryl group, for example phenyl or benzyl; or (~X—R8), with the provision that no more than 2 of the groups R5, R6 or R7 can stand for (~X—R8), wherein X has the following meaning: —(CH2)n- with n=1 to 20, preferably n=1 to 10 and particularly preferably n=1 to 5; —(CH$_2$—CHR9-O)$_n$— with n=1 to 200, preferably 1 to 100, more preferably 1 to 50, and particularly preferably 1 to 20, and also with R9 meaning hydrogen, methyl or ethyl; or a hydroxyalkylene group having one to four carbon atoms, which can be branched or unbranched and which includes at least one and at most 3 hydroxyl groups, and wherein R8 has the following meaning: R10-O—CO—, in which R10 is a saturated or unsaturated, branched or unbranched or a cyclic, saturated or unsaturated alkyl group having 6 to 30 carbon atoms, which can include at least one hydroxyl group and which optionally can also be ethoxylated with 1 to 100 ethylene oxide units and/or 1 to 100 propylene oxide units; or R11-CO—, in which R11 is a saturated or unsaturated, branched or unbranched or a cyclic, saturated or unsaturated alkyl group having 6 to 30 carbon atoms, which can include at least one hydroxyl group and which optionally can also be ethoxylated with 1 to 100 ethylene oxide units and/or 1 to 100 propylene oxide units, and in which A stands for a physiologically acceptable organic or inorganic anion, one of the groups R5, R6 or R7 preferably stands for the group (~X—R8), R8 stands for a non-ethoxylated fatty acid group, such as a palmitic, stearic, arachinic or a behenic acid group, in particular a stearic acid group, and A stands for a halide ion, a sulfate ion of general formula $RSO_3-$, in which R means saturated or unsaturated alkyl groups having 1 to 4 carbon atoms, or stands for an anionic group of an organic acid such as maleic acid, fumaric acid, oxalic acid, tartaric acid, citric acid, lactic acid, or acetic acid, in particular for a chloride ion or for a methosulfate ion.

The esterquats suitable for the agents according to the invention are preferably selected from at least one of the products marketed under the trade names Rewoquat®, Stepantex®, Dehyquart®, Armocare® and Akypoquat®. Specific examples of esterquats that are particularly suitable in accordance with the invention are the products Armocare® VGH-70, Dehyquart® F-75, Dehyquart® C-4046, Dehyquart® L80, Dehyquart® F-30, Dehyquart® AU-35, Rewoquat® WE18, Rewoquat® WE38 DPG, Stepantex® VS 90 and Akypoquat® 131.

Particularly preferred agents according to the invention include, as esterquat, at least one of the compounds known under the INCI names Distearoylethyl Hydroxyethylmonium Methosulfate and Distearoylethyl Hydroxyethylmonium Chloride.

Distearoylethyl Hydroxyethylmonium Methosulfate is particularly preferred and can be included in the agents according to the invention in a preferred amount of from 0.1 to 10% by weight, more preferably from 0.5 to 8% by weight, particularly preferred from 0.75 to 6% by weight, and in particular from 1 to 5% by weight, wherein the specified amounts relate to the total weight of the agent according to the invention.

The esterquat(s) can be added to the agents according to the invention either individually or as a mixture with other nourishing active substances.

Due to the improved handling and processability, it may be advantageous when the esterquat(s)—in particular Distearoylethyl Hydroxyethylmonium Methosulfate—is/are added to the agents according to the invention as an active substance mixture. A particularly suitable example for an active substance mixture of this type is obtainable for example under the trade name Dehyquart® F 75 from the company BASF (Distearoylethyl Hydroxyethylmonium Methosulfate and Cetearyl Alcohol).

The hair treatment agents include at least one aminofunctional silicone.

Such silicones can be described for example by the formula

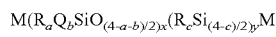

$M(R_aQ_bSiO_{(4-a-b)/2})_x(R_cSi_{(4-c)/2})_yM$ wherein, in the above formula, R is a hydrocarbon or a hydrocarbon group having 1 to approximately 6 carbon atoms, Q is a polar group of general formula —R$^1$HZ, in which R$^1$ is a bivalent, linking group bonded to hydrogen and the group Z, composed of carbon and hydrogen atoms, carbon, hydrogen and oxygen atoms, or carbon, hydrogen and nitrogen atoms, and Z is an organic, aminofunctional group including at least one aminofunctional group; "a" assumes values in a range of from approximately 0 to approximately 2, "b" assumes values in a range of from approximately 1 to approximately 3, "a"+"b" is less than or equal to 3, and "c" is a number in a range of from approximately 1 to approximately 3, and x is a number in a range of from 1 to approximately 2,000, preferably from approximately 3 to approximately 50, and most preferably from approximately 3 to approximately 25, and y is a number in a range of from approximately 20 to approximately 10,000, preferably from approximately 125 to approximately 10,000, and most preferably from approximately 150 to approximately 1,000, and M is a suitable silicone end group as is known in the prior art, preferably trimethylsiloxy. Non-limiting examples of the groups represented by R include alkyl groups, such as methyl, ethyl, propyl, isopropyl, isopropyl, butyl, isobutyl, amyl, isoamyl, hexyl, isohexyl and the like; alkenyl groups such as vinyl, halogenvinyl, alkylvinyl, allyl, halogenallyl, alkylallyl; cycloalkyl groups such as cyclobutyl, cyclopentyl, cyclohexyl and the like; phenyl groups, benzyl groups, halogen hydrocarbon groups, such as 3-chloropropyl, 4-bromobutyl, 3,3,3-trifluoropropyl, chlorocyclohexyl, bromophenyl, chlorophenyl and the like, and also sulfurous groups, such as mercaptoethyl, mercaptopropyl, mercaptohexyl, mercaptophenyl and the like; R is preferably an alkyl group including 1 to approximately 6 carbon atoms, and R is most preferably methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$ CC(O)OCH$_2$CH$_2$—, —C$_6$H$_4$C$_6$H$_4$—, —C$_6$H$_4$CH$_2$C$_6$H$_4$—, and —(CH$_2$)$_3$C(O)SCH$_2$CH$_2$—.

Z is an organic aminofunctional group, including at least one functional amino group. A possible formula for Z is NH(CH$_2$)$_z$NH$_2$, in which z is 1 or more. Another possible formula for Z is —NH(CH$_2$)$_z$(CH$_2$)$_{zz}$NH, in which both z and zz, independently, are 1 or more, wherein this structure includes diamino ring structures, such as piperazinyl. Z is most preferably a —NHCH$_2$CH$_2$NH$_2$— group. Another possible formula for Z is —N(CH$_2$)$_z$(CH$_2$)$_{zz}$NX$_2$ or —NX$_2$, in which each X of X$_2$ is selected independently from the group consisting of hydrogen and alkyl groups having 1 to 12 carbon atoms, and zz is 0.

Q is most preferably a polar aminofunctional group of formula —CH$_2$CH$_2$CH$_2$NHCH$_2$CH$_2$NH$_2$. In the formulas, "a" assumes values in a range of from approximately 0 to approximately 2, "b" assumes values in a range of from approximately 2 to approximately 3, "a"+"b" is less than or equal to 3, and "c" is a number in a range of from approximately 1 to approximately 3. The molar ratio of R$_a$Q$_b$ SiO$_{(4-a-b)/2}$ units to the R$_c$SiO$_{(4-c)/2}$ units lies in a range of from approximately 1:2 to 1:65, preferably from approximately 1:5 to approximately 1:65, and most preferably from approximately 1:15 to approximately 1:20. If one or more silicones of the above formula is/are used, the various variable substituents in the above formula are different in the various silicone components present in the silicone mixture.

Preferred agents according to the invention are characterized in that they include an aminofunctional silicone of formula (Si-II)

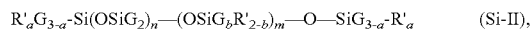

$R'_aG_{3-a}\text{-}Si(OSiG_2)_n\text{—}(OSiG_bR'_{2-b})_m\text{—}O\text{—}SiG_{3-a}\text{-}R'_a$ (Si-II), in which: G is —H, a phenyl group, —OH, —O—CH$_3$, —CH$_3$, —O—CH$_2$CH$_3$, —CH$_2$CH$_3$, —O—CH$_2$CH$_2$CH$_3$, —CH$_2$CH$_2$CH$_3$, —O—CH(CH$_3$)$_2$, —CH(CH$_3$)$_2$, —O—CH$_2$CH$_2$CH$_2$CH$_3$, —CH$_2$CH$_2$CH$_2$CH$_3$, —O—CH$_2$CH(CH$_3$)$_2$, —CH$_2$CH(CH$_3$)$_2$, —O—CH(CH$_3$)CH$_2$CH$_3$, —CH(CH$_3$)CH$_2$CH$_3$, —O—C(CH$_3$)$_3$, and/or —C(CH$_3$)$_3$, a is a number between 0 and 3, in particular 0; b is a number between 0 and 1, in particular 1; m and n are numbers of which the sum (m+n) is between 1 and 2000, preferably between 50 and 150, wherein n preferably assumes values from 0 to 1999 and in particular from 49 to 149 and m preferably assumes values from 1 to 2000, in particular from 1 to 10; R' is a monovalent group selected from: -Q-N(R'')—CH$_2$—CH$_2$—N(R'')$_2$, -Q-N(R'')$_2$, -Q-N$^+$(R'')$_3$A$^-$, -Q-N$^+$ H(R'')$_2$A$^-$, -Q-N$^+$ H$_2$(R'')A$^-$, and/or -Q-N(R'')—CH$_2$—CH$_2$—N$^+$ R''H$_2$A$^-$, wherein each Q stands for a chemical bond, —CH$_2$—, —CH$_2$—CH$_2$—, —CH$_2$CH$_2$CH$_2$—, —C(CH$_3$)$_2$—, —CH$_2$CH$_2$CH$_2$CH$_2$—, —CH$_2$C(CH$_3$)$_2$—, and/or —CH(CH$_3$)CH$_2$CH$_2$—, and R'' stands for the same or different groups from the group comprising —H, -phenyl, -benzyl, —CH$_2$—CH(CH$_3$)Ph, and/or C$_{1-20}$ alkyl groups, preferably —CH$_3$, —CH$_2$CH$_3$, —CH$_2$CH$_2$CH$_3$, —CH(CH$_3$)$_2$, —CH$_2$CH$_2$CH$_3$, —CH$_2$CH(CH$_3$)$_2$, —CH(CH$_3$)CH$_2$CH$_3$, and/or —C(CH$_3$)$_3$, and A represents an anion preferably selected from chloride, bromide, iodide or methosulfate.

Particularly preferred agents according to the invention are characterized in that they include at least one aminofunctional silicone of formula (Si-IIa)

(Si-IIa)

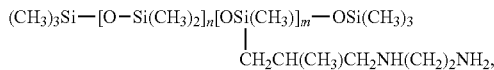

in which m and n are numbers of which the sum (m+n) is between 1 and 2000, preferably between 50 and 150, wherein n preferably assumes values from 0 to 1999 and in particular from 49 to 149, and m preferably assumes value from 1 to 2000, in particular from 1 to 10.

These silicones are called Trimethylsilylamodimethicones in accordance with the INCI declaration.

Particularly preferred agents according to the invention are also those that include an aminofunctional silicone of formula (Si-IIb)

(Si-IIb)

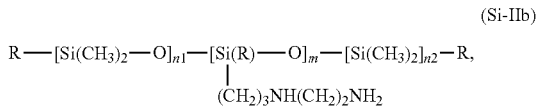

in which R stands for —OH, —O—CH$_3$ or a —CH$_3$ groups and m, n1 and n2 are numbers of which the sum (m+n1+n2) is between 1 and 2000, preferably between 50 and 150, wherein the sum (n1+n2) preferably assumes values from 0 to 1999 and in particular from 49 to 149, and m preferably assumes values from 1 to 2000, in particular from 1 to 10.

These silicones are referred to as Amodimethicones in accordance with the INCI declaration.

Regardless of which aminofunctional silicones are used, agents according to the invention that include an aminofunctional silicone of which the amine value is above 0.25 meq/g, preferably above 0.3 meq/g, and in particular above 0.4 meq/g, are preferred. The amine value stands for the milli-equivalent amine per gram of aminofunctional silicone. It can be determined by titration and can also be specified in the unit mg KOH/g.

Hair treatment agents that are preferred in accordance with the invention are characterized in that they include, in relation to the weight of the agent, 0.01 to 20% by weight, preferably 0.1 to 10% by weight, more preferably 0.5 to 7.5% by weight, and in particular 1 to 5% by weight of aminofunctional silicone(s).

The agents according to the invention particularly preferably include aminofunctional silicone(s) with terminal hydroxyl group(s). Some specific aminofunctional silicone(s) with terminal hydroxyl group(s) have proven to be particularly suitable in the agents according to the invention. These will be described further below.

Agents that are preferred in accordance with the invention are characterized in that they include, in relation to their weight, 0.01 to 20% by weight, preferably 0.1 to 10% by weight, particularly preferably 0.5 to 7.5% by weight, and in particular 1 to 5% by weight, of at least one silicone of the following formula (Si-III)

(Si-III)

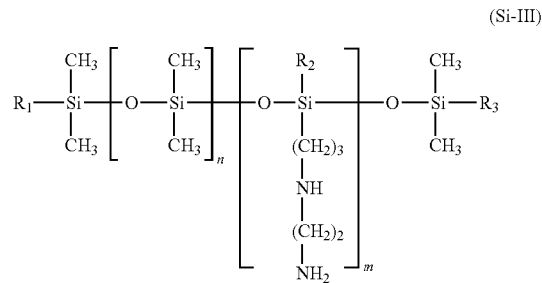

in which: m and n are numbers which are selected so that the sum (n+m) lies in a range of from 1 to 1000; n is a number in the range of from 0 to 999; m is a number in the range of from 1 to 1000; R1, R2, and R3, which are the same or different, are selected from a hydroxyl group or a C$_1$-4 alkoxy group, wherein at least one of the groups R1, R2, and R3 is a hydroxyl group.

Further agents that are preferred in accordance with the invention are characterized in that they include, in relation to their weight, 0.01 to 20% by weight, preferably 0.1 to 10% by weight, particularly preferably 0.5 to 7.5% by weight, and in particular 1 to 5% by weight, of at least one silicone of the formula below (Si-IV)

(Si-IV)

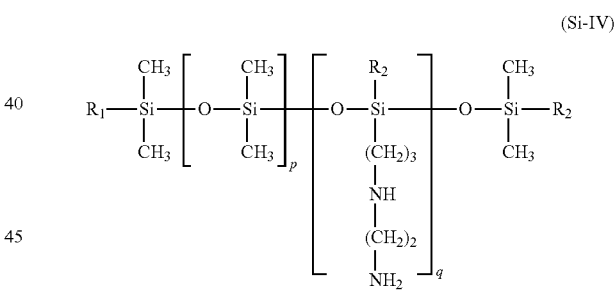

in which: p and q are numbers such that the sum (p+q) lies in a range of from 1 to 1000; p is a number in the range of from 0 to 999; q is a number in the range of from 1 to 1000; R1 and R2, which are different and selected from: a hydroxyl group or a C1-4 alkoxy group, wherein at least one of the groups R1 or R2 is a hydroxyl group.

The silicones of formulas (Si-III) and (Si-IV) differ by the grouping at the Si atom, which carries the nitrogen-including group. In formula (Si-III), R2 is a hydroxyl group or C1-4 alkoxy group, whereas the group in formula (Si-IV) is a methyl group. The individual Si groupings, which are characterized by the indices m and n and also p and q, need not be present as blocks. Rather the individual units may also be randomly distributed, i.e., in the formulas (Si-III) and (Si-IV) each R1-Si(CH$_3$)$_2$ group is not necessarily bonded to a —[O—Si(CH$_3$)$_2$] grouping.

In the method according to the invention, pre-treatment agents that are particularly effective in respect of the desired effects have proven to be those that include at least one silicone of the formula (Si-V):

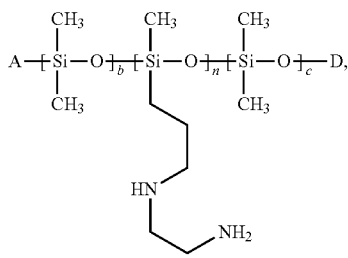

(Si-V)

in which: A is a group selected from: —OH, —O—Si(CH$_3$)$_3$, —O—Si(CH$_3$)$_2$OH, and —O—Si(CH$_3$)$_2$OCH$_3$, D is a group selected from: —H, —Si(CH$_3$)$_3$, —Si(CH$_3$)$_2$OH, and —Si(CH$_3$)$_2$OCH$_3$, b, n, and c are integers between 0 and 1000, such that n>0, b+c>0, and at least one of the conditions A=—OH or D=—H is met.

Hair treatment agents according to the invention that include, in relation to their weight, 0.01 to 20% by weight, preferably 0.1 to 10% by weight, particularly preferably 0.5 to 7.5% by weight, and in particular 1 to 5% by weight, of at least one silicone of formula (Si-V)

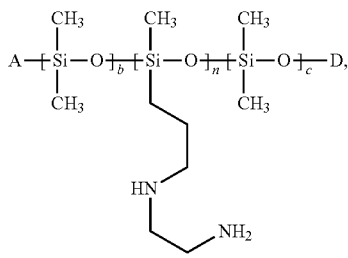

(Si-V)

in which: A is a group selected from: —OH, —O—Si(CH$_3$)$_3$, —O—Si(CH$_3$)$_2$OH, and —O—Si(CH$_3$)$_2$OCH$_3$, D is a group selected from: —H, —Si(CH$_3$)$_3$, —Si(CH$_3$)$_2$OH, and —Si(CH$_3$)$_2$OCH$_3$, b, n, and c are integers between 0 and 1000, such that n>0, b+c>0, and at least one of the conditions A=—OH or D=—H is met, are therefore preferred in accordance with the invention.

In the above formula (Si-V), the individual siloxane units with the indices b, c and n may be randomly distributed, i.e., they are not necessarily block copolymers.

Further particularly preferred silciones are 4-morpholinomethyl-substituted. Hair treatment agents according to the invention which, in relation to their weight, include 0.01 to 20% by weight, preferably 0.1 to 10% by weight, particularly preferably 0.5 to 7.5% by weight, and in particular 1 to 5% by weight, of at least one 4-morpholinomethyl-substituted silicone of formula (Si-VI),

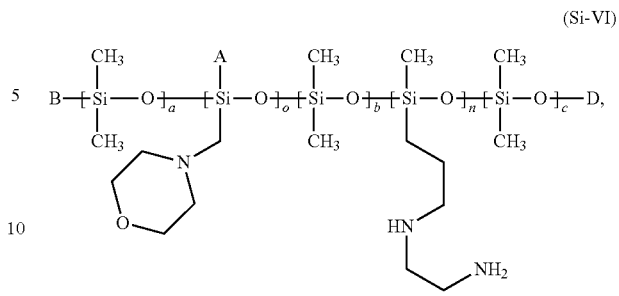

(Si-VI)

in which: A is a structural unit (i) bonded via an —O

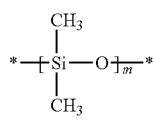

(i)

or for an oligomeric or polymeric group bonded via an —O and including structural units of the formula (i), or stands for —OH; * is a bond to the structural unit (i) or stands for an end group B (Si-bonded) or D (O-bonded); B is a group selected from: —OH, —O—Si(CH$_3$)$_3$, —O—Si(CH$_3$)$_2$OH, and —O—Si(CH$_3$)$_2$OCH$_3$, D is a group selected from: —H, —Si(CH$_3$)$_3$, —Si(CH$_3$)$_2$OH, and —Si(CH$_3$)$_2$OCH$_3$, a, b, and c are integers between 0 and 1000, such that a+b+c>0; m, n, and o are integers between 1 and 1000; with the provision that at least one of the conditions B=—OH or D=—H is met, are particularly preferred.

The structural formula (Si-VI) is intended to indicate that the siloxane groups n and o need not be directly bonded to an end grouping B or D respectively. Rather, in preferred formulas (Si-VI) a>0 or b>0 and in particularly preferred formulas (Si-VI) a>0 and b>0, i.e. the end grouping B or D is preferably bonded to a dimethylsiloxy grouping. In formula (Si-VI) as well, the siloxane units a, b, c, n and o are preferably randomly distributed. The silicones used in accordance with the invention presented by formula (Si-VI) may be trimethylsilyl-terminated (D or B=—Si(CH$_3$)$_3$), but they may be dimethylsilylhydroxy-terminated at two ends or dimethylsilylhydroxy-terminated and dimethylsilylmethoxy-terminated at one end. Silicones used with particular preference within the scope of the present invention are selected from silicones in which:

B=—O—Si(CH$_3$)$_2$OH and D=—Si(CH$_3$)$_3$,

B=—O—Si(CH$_3$)$_2$OH and D=—Si(CH$_3$)$_2$OH,

B=—O—Si(CH$_3$)$_2$OH and D=—Si(CH$_3$)$_2$OCH$_3$,

B=—O—Si(CH$_3$)$_3$ and D=—Si(CH$_3$)$_2$OH, and/or

B=—O—Si(CH$_3$)$_2$OCH$_3$ and D=—Si(CH$_3$)$_2$OH.

These silicones lead to enormous improvements of the hair properties of the hair treated using the agents according to the invention, and in particular lead to a significantly improved protection in the case of oxidative treatment.

In formula (Si-VI) as well, the group A may be: a structural unit (i) bonded via an —O; an oligomeric or polymeric group bonded via an —O and including structural units of formula (i); or —OH.

Formula (Si-VI) is thus rendered more precisely as one of the formulas (Si-VIa), (Si-VIb) or (Si-VIc):

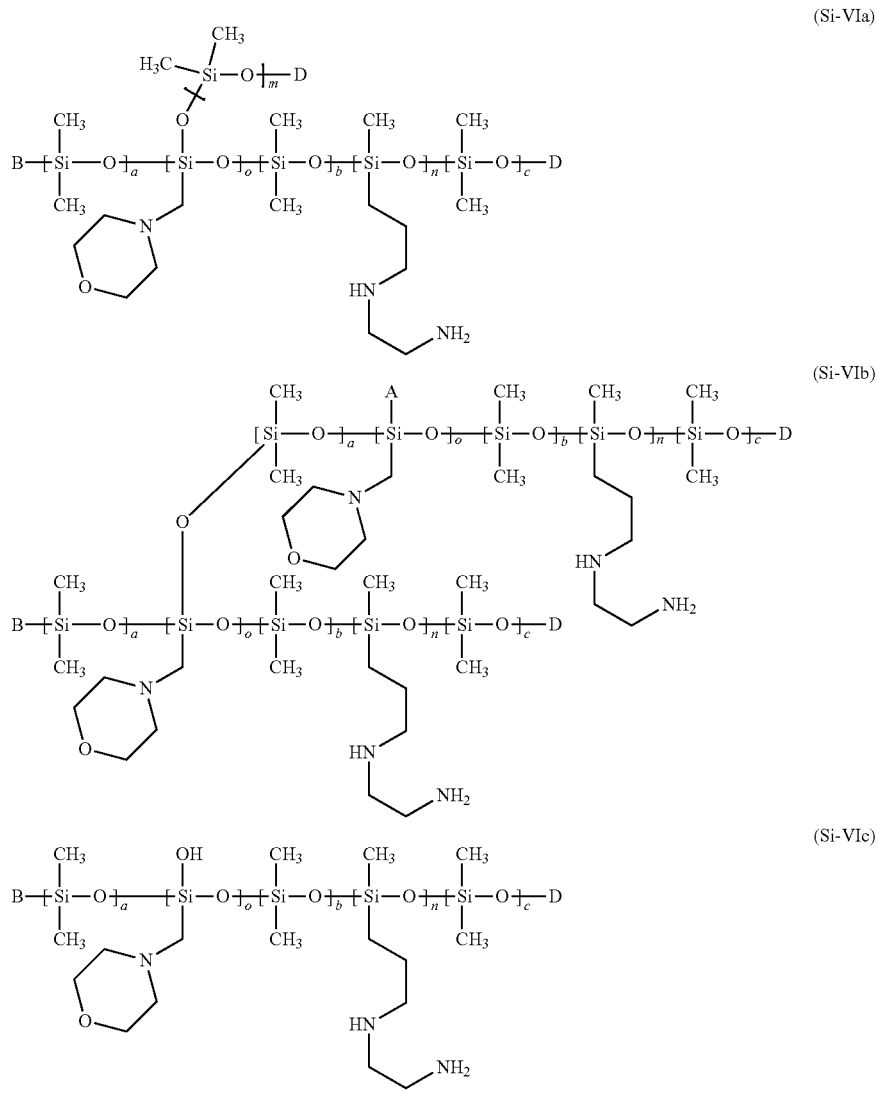

Regardless of the type of used aminofunctional silicone(s) with terminal hydroxyl group(s), the agents according to the invention preferably include the silicone(s) in the form of an emulsion, particularly preferably in the form of a microemulsion.

It has been found that the effect of the silicones used in the agents according to the invention can be increased further still if certain non-ionic components are also used in the agents. In addition, these non-ionic components have positive effects on the storage stability of the agents. Non-ionic components which are particularly suitable here are ethoxylates of decanol, undecanol, dodecanol, tridecanol etc. Ethoxylated tridecanols have proven to be particularly suitable and are preferably incorporated into the agents according to the invention. Agents that are particularly preferred in accordance with the invention are characterized in that they include, in relation to the weight of the agent, 0.00001 to 5% by weight, preferably 0.0001 to 3.5% by weight, particularly preferably 0.001 to 2% by weight, more preferably 0.01 to 1% by weight, and in particular 0.1 to 0.5% by weight of branched ethoxylated tridecanol (INCI name: Trideceth-5) or α-iso-tridecyl-w-hydroxy polyglycol ether (INCI name: Trideceth-10) or mixtures thereof.

The hair treatment agents according to the invention include o-Cymen-5-ol. This compound is also referred to as cymenol or 4-isopropyl-m-cresol and is preferably used within specific relatively narrow limits. Hair treatment agents that are preferred in accordance with the invention include, in relation to the weight of the agent, 0.001 to 0.4% by weight, preferably 0.01 to 0.3% by weight, more preferably 0.025 to 0.2% by weight, and in particular 0.5 to 0.1% by weight of o-Cymen-5-ol.

The hair treatment agents according to the invention include phenoxyethanol. Phenoxyethanol is also preferably used within specific relatively narrow limits. Hair treatment agents that are preferred in accordance with the invention include, in relation to the weight of the agent, 0.01 to 5% by weight, preferably 0.025 to 3% by weight, more preferably 0.05 to 2% by weight, and in particular 0.1 to 1% by weight of phenoxyethanol.

The hair treatment agents include the above-described active substances preferably in a cosmetically acceptable carrier. Within the scope of the invention, an aqueous or aqueous-alcoholic carrier is meant hereby.

The cosmetic carrier preferably includes at least 50% by weight, more preferably at least 60% by weight, particularly preferably at least 70% by weight, and especially preferably at least 75% by weight of water. Additionally, the cosmetic carrier may include 0.01 to 40% by weight, preferably 0.05 to 30% by weight, and in particular 0.1 to 20% by weight of at least one alcohol.

Suitable alcohols include, for example, ethanol, ethyldiglycol, 1-propanol, 2-propanol, isopropanol, 1,2-propylene glycol, glycerol, diglycerol, triglycerol, 1-butanol, 2-butanol, 1,2-butanediol, 1,3-butanediol, 1-pentanol, 2-pentanol, 1,2-pentanediol, 1,5-pentanediol, 1, hexanol, 2-hexanol, 1,2-hexanediol, 1,6-hexanediol, polyethylene glycols, sorbitol, sorbitan, benzyl alcohol or mixtures of these alcohols.

The water-soluble alcohols are particularly preferred. Ethanol, 1,2-propylene glycol, glycerol, benzyl alcohol and mixtures of these alcohols are preferred in particular.

For very good skin (scalp) compatibility of the hair treatment agents according to the invention, it is advantageous if said agents have a slightly acidic pH value. It has been found that the agents according to the invention have particularly good skin compatibility and gentleness in a pH range of from 4.2 to 5.8.

In a first preferred embodiment the hair treatment agents according to the invention therefore preferably have a pH value in a range of from 4.2 to 5.8, more preferably of from 4.25 to 5.6, particularly preferably of from 4.3 to 5.5, extremely preferably of from 4.35 to 5.4, and especially preferably of from 4.4 to 5.3.

The hair treatment agents according to the invention can include vegetable oils, vegetable butters, and/or vegetable waxes. These vegetable oil components provide the hair with improved combability and manageability and increase the shine of the hair.

Suitable vegetable oil components include natural (vegetable) oils and/or butters, which typically include triglycerides and mixtures of triglycerides.

Preferred natural oils are coconut oil, (sweet) almond oil, walnut oil, peach kernel oil, apricot kernel oil, argan oil, avocado oil, tea tree oil, soybean oil, sesame oil, sunflower oil, tsubaki oil, evening primrose oil, rice bran oil, palm kernel oil, mango kernel oil, marula oil, lady's smock oil, thistle oil, macadamia nut oil, grape seed oil, amaranth seed oil, bamboo oil, olive oil, wheatgerm oil, pumpkin seed oil, mallow oil, hazelnut oil, safflower oil, canola oil, sasanqua oil, jojoba oil, rambutan oil, cocoa butter, and/or shea butter.

Carnauba wax, beeswax, and/or candelilla wax can be used with preference as suitable natural or vegetable wax.

Particularly preferred vegetable oil components are (sweet) almond oil, peach kernel oil, apricot kernel oil, amaranth seed oil, argan oil, olive oil, jojoba oil, cocoa butter, and/or shea butter. Apricot kernel oil, argan oil, olive oil, and/or jojoba oil are particularly preferred.

In a preferred embodiment the hair treatment agents according to the invention preferably include coconut oil, (sweet) almond oil, walnut oil, peach kernel oil, apricot kernel oil, argan oil, avocado oil, tea tree oil, soybean oil, sesame oil, sunflower oil, tsubaki oil, evening primrose oil, rice bran oil, palm kernel oil, mango kernel oil, marula oil, lady's smock oil, thistle oil, macadamia nut oil, grape seed oil, amaranth seed oil, bamboo oil, olive oil, wheatgerm oil, pumpkin seed oil, mallow oil, hazelnut oil, safflower oil, canola oil, sasanqua oil, jojoba oil, rambutan oil, cocoa butter, and/or shea butter.

Within this embodiment it is particularly preferred if the hair treatment agents according to the invention include (sweet) almond oil, peach kernel oil, apricot kernel oil, amaranth seed oil, argan oil, olive oil, jojoba oil, cocoa butter, and/or shea butter.

The weight share of the at least one vegetable oil, the vegetable butter and/or the vegetable wax in the total weight of the hair treatment agent according to the invention is preferably 0.02 to 2.50% by weight, more preferably from 0.03 to 2.00% by weight, particularly preferably 0.04 to 1.50% by weight, and in particular 0.05 to 1.00% by weight.

Besides the aforementioned essential and optional constituents, the hair treatment agents according to the invention, in a further preferred embodiment for further increasing the nourishing properties of the agents, can include at least one further hair-conditioning active substance, which can be selected from: protein hydrolyzates, vitamins, plant extracts, and/or glycerol.

Suitable protein hydrolyzates are to be understood to be product mixtures that can be obtained by acid-, base- or enzyme-catalyzed degradation of proteins. Protein hydrolyzates of plant, animal, and/or marine origin may be used.

Animal protein hydrolyzates are, for example, elastin, collagen, keratin, silk and milk protein hydrolyzates, which can also be present in the form of salts. Such products are marketed for example under the trade names Dehylan® (Cognis), Promois® (Interorgana) Collapuron® (Cognis), Nutrilan® (Cognis), Gelita-Sol® (German gelatin factories Stoess & Co), Lexein® (Inolex), and Kerasol® (Croda).

Protein hydrolyzates of plant origin are preferred, for example, soy, almond, rice, pea, potato and wheat protein hydrolyzates. Such products are obtainable, for example, under the trade names Gluadin® (Cognis), DiaMin® (Diamalt), Lexenin® (Inolex), and Crotein® (Croda).

In addition, cationized protein hydrolyzates can be used, wherein the basic protein hydrolyzate can originate from animals, for example, from collagen, milk or keratin, from plants, for example, from wheat, maize, rice, potatoes, soya or almonds, from marine life, for example, from fish collagen or algae, or from biotechnologically obtained protein hydrolyzates. The protein hydrolyzates forming the basis of the cationic derivatives can be obtained from the corresponding proteins by a chemical hydrolysis, particularly alkaline or acid hydrolysis, by an enzymatic hydrolysis and/or a combination of both types of hydrolysis. The hydrolysis of proteins generally produces a protein hydrolyzate with a molecular weight distribution from about 100 daltons up to several thousand daltons. Cationic protein hydrolyzates that are preferred are those of which the base protein content has a molecular weight of 100 to 25,000 daltons, preferably 250 to 5,000 daltons. Moreover, cationic protein hydrolyzates are understood to include quaternized amino acids and their mixtures. Quaternization of the protein hydrolyzates or the amino acids is often carried out using quaternary ammonium salts such as, for example, N,N-dimethyl-N-(n-alkyl)-N-(2-hydroxy-3-chloro-n-propyl) ammonium halides. Moreover, the cationic protein hydrolyzates can also be further derivatized. Typical examples of cationic protein hydrolyzates and derivatives are the commercially available products known under the INCI names Cocodimonium Hydroxypropyl Hydrolyzed Collagen, Cocodimopnium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, and Quaternium-79 Hydrolyzed Wheat Protein.

The weight share of the protein hydrolyzate(s) in the total weight of the hair treatment agent is preferably 0.01 to 5% by weight, more preferably 0.025 to 3% by weight, and in particular 0.05 to 2% by weight.

Regardless of the source (plant, animal, marine, etc.), protein hydrolyzates include individual amino acids, oligopeptides and optionally polypeptides depending on the degree of hydrolysis.

The hair treatment agents according to the invention preferably include at least one oligopeptide which includes at least one amino acid sequence Glu-Glu-Glu

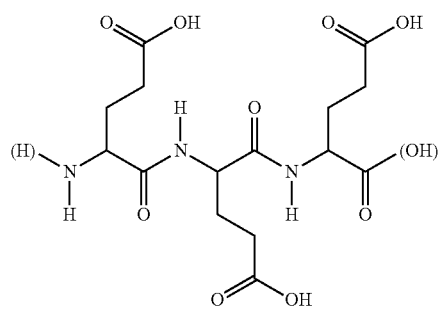

wherein the amino group can be free or protonated and the carboxyl group can be free or deprotonated.

Preferred hair treatment agents according to the invention are characterized in that they include, in relation to the weight of the agent, 0.0001 to 10% by weight of at least one oligopeptide which includes at least one amino acid sequence Glu-Glu-Glu

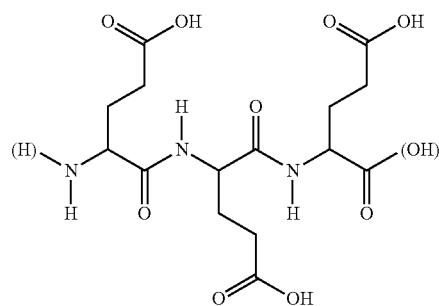

wherein the amino group can be free or protonated and the carboxyl group can be free or deprotonated.

In these formulas, as in all preceding formulas, the bracketed hydrogen atom of the amino group (H) and also the bracketed hydroxyl group of the acid function (OH) indicate that the groups in question may be present as such (then, it is an oligopeptide having the relevant number of amino acids as illustrated (in formula 3 above)), or that the amino acid sequence is present in an oligopeptide which also includes further amino acids—depending on where the further amino acid(s) is/are bonded, the bracketed constituents of the above-mentioned formula are replaced by the further amino acid group(s).

These preferred hair treatment agents according to the invention include, in relation to the weight of the agent, 0.0001 to 10% by weight of at least one oligopeptide which includes at least one amino acid sequence Glu-Glu-Glu, i.e., at least three successive glutaminic acids.

Oligopeptides in the sense of the present application are condensation products of amino acids linked in an acid amide-like manner by peptide bonds and comprising at least 3 and at most 25 amino acids.

In preferred hair treatment agents according to the invention the oligopeptide has 5 to 15 amino acids, preferably 6 to 13 amino acids, particularly preferably 7 to 12 amino acids, and in particular 8, 9 or 10 amino acids.

Depending on whether further amino acids are bonded to the sequence Glu-Glu-Glu and depending on the type of these amino acids, the molar mass of the oligopeptide included in the agents according to the invention can vary. Hair treatment agents used with preference in accordance with the invention are characterized in that the oligopeptide has a molar mass of from 650 to 3000 daltons, preferably from 750 to 2500 daltons, particularly preferably from 850 to 2000 daltons, and in particular from 1000 to 1600 daltons.

To summarize, preferred hair treatment agents are characterized in that the oligopeptide has 5 to 15 amino acids, preferably 6 to 13 amino acids, particularly preferably 7 to 12 amino acids, and in particular 8, 9 or 10 amino acids, and has a molar mass of from 650 to 3000 daltons, preferably from 750 to 2500 daltons, particularly preferably from 850 to 2000 daltons, and in particular from 1000 to 1600 daltons.

As is clear from the preferred number of amino acids in the oligopeptides and the preferred molar mass range, oligopeptides which do not consist solely of the three glutaminic acids, but which include further amino acids bonded to this sequence are preferably used. These further amino acids are preferably selected from certain amino acids, whereas certain other representatives are less preferred in accordance with the invention.

It is thus preferred when the oligopeptides used in the agents according to the invention do not include any methionine. It is more preferred when the oligopeptides used in the agents according to the invention do not include any cysteine and/or cystine. It is more preferred when the oligopeptides used in the agents according to the invention do not include any aspartic acid and/or asparagine. It is more preferred when the oligopeptides used in the agents according to the invention do not include any serine and/or threonine.

By contrast, it is preferred when the oligopeptides used in the agents according to the invention include tyrosine. It is more preferred when the oligopeptides used in the agents according to the invention include leucine. It is more preferred when the oligopeptides used in the agents according to the invention include isoleucine. It is more preferred when the oligopeptides used in the agents according to the invention include arginine. It is more preferred when the oligopeptides used in the agents according to the invention include valine.

Particularly preferred oligopeptides or amino acid sequences included in the preferred oligopeptides will be described below:

A particularly preferred oligopeptide additionally includes tyrosine, which is preferably bonded via its acid function to the Glu-Glu-Glu sequence. Hair treatment agents that are preferred in accordance with the invention are therefore characterized in that the oligopeptide includes therein includes at least one amino acid sequence SEQ. ID No.: 1 Tyr-Glu-Glu-Glu are therefore characterized in that the oligopeptide includes therein includes at least one amino acid sequence SEQ. ID No.: 2 Glu-Glu-Glu-Ile

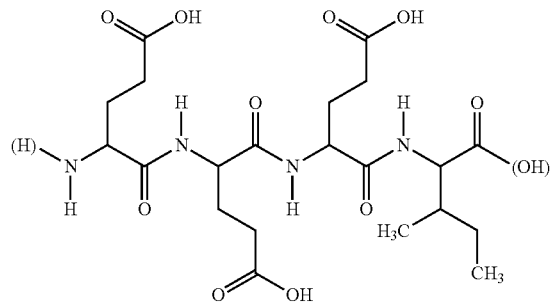

wherein the amino group can be free or protonated and the carboxyl group can be free or deprotonated.

Oligopeptides that include both aforementioned amino acids (tyrosine and isoleucine) are preferred in accordance with the invention. Here, hair treatment agents according to the invention that are particularly preferred are those in which the oligopeptide included in the hair treatment agent includes at least one amino acid sequence SEQ. ID No.: 3 Tyr-Glu-Glu-Glu-Ile

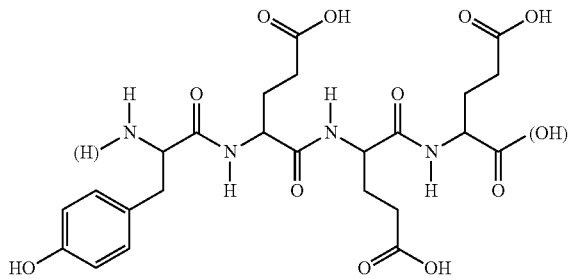

wherein the amino group can be free or protonated and the carboxyl group can be free or deprotonated.

A further particularly preferred oligopeptide additionally include isoleucine, which is preferably bonded via its amino acid function to the Glu-Glu-Glu sequence. Hair treatment agents that are preferred in accordance with the invention

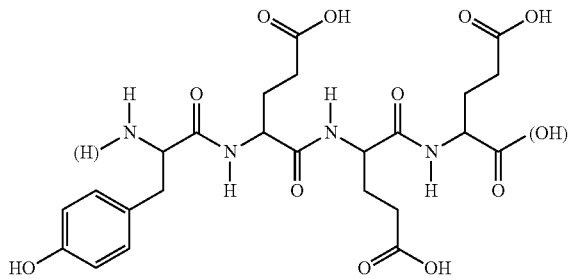

wherein the amino group can be free or protonated and the carboxyl group can be free or deprotonated.

Oligopeptides that are more preferred additionally include arginine which is preferably bonded to isoleucine. Here, hair treatment agents according to the invention that are particularly preferred are those in which the oligopeptide included in the hair treatment agent includes at least one amino acid sequence SEQ. ID No.: 4 Tyr-Glu-Glu-Glu-Ile-Arg

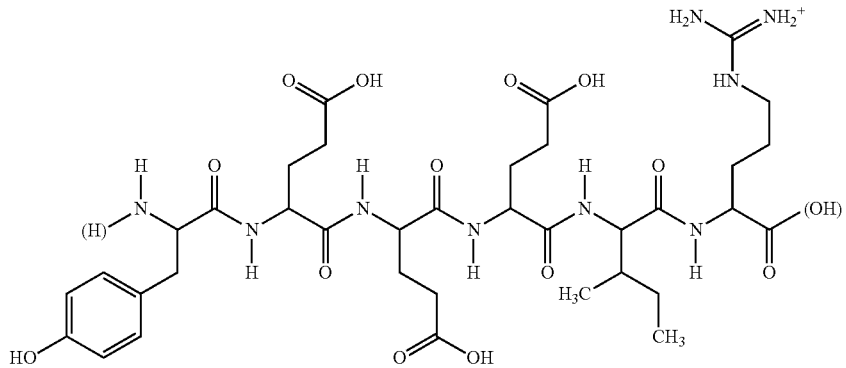

wherein the amino groups can be free or protonated and the carboxyl groups can be free or deprotonated.

Oligopeptides that are even more preferred additionally include valine which is preferably bonded to the arginine. Hair treatment agents that are more preferred in accordance with the invention are therefore characterized in that the oligopeptide included in the hair treatment agent includes at least one amino acid sequence SEQ. ID No.: 5 Tyr-Glu-Glu-Glu-Ile-Arg-Val

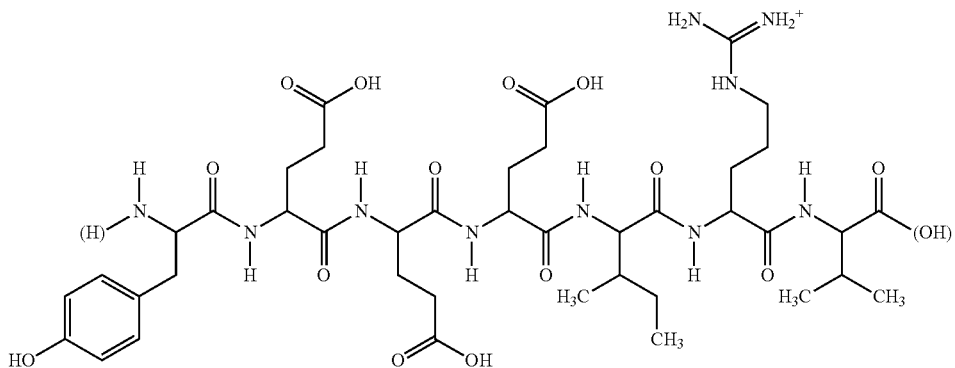

wherein the amino groups can be free or protonated and the carboxyl group can be free or deprotonated.

Oligopeptides that are even more preferred additionally include leucine which is preferably bonded to the valine. Hair treatment agents that are more preferred in accordance with the invention are therefore characterized in that the oligopeptide included in the hair treatment agent includes at least one amino acid sequence SEQ. ID No.: 6 Tyr-Glu-Glu-Glu-Ile-Arg-Val-Leu

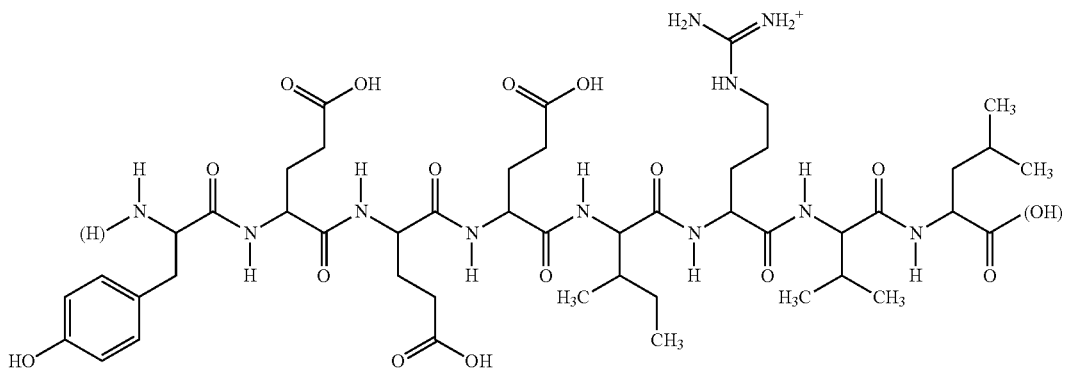

wherein the amino groups can be free or protonated and the carboxyl groups can be free or deprotonated.

Particularly preferred oligopeptides additionally include leucine which is preferably bonded to the tyrosine. Hair treatment agents that are more preferred in accordance with the invention are therefore characterized in that the oligopeptide included in the hair treatment agent includes at least one amino acid sequence SEQ. ID No.: 7 Leu-Tyr-Glu-Glu-Glu-Ile-Arg-Val-Leu

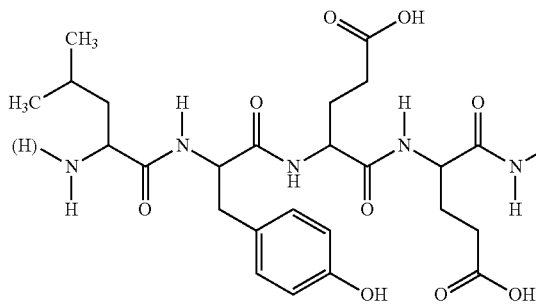
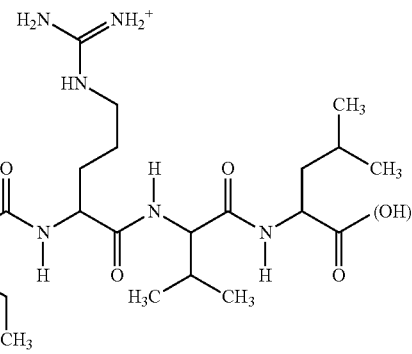

wherein the amino groups can be free or protonated and the carboxyl groups can be free or deprotonated.

Agents according to the invention very particularly preferably include at least two oligopeptides which meet the above-mentioned criteria, but are different from one another. By way of example, the use of hair treatment agents that include at least two different oligopeptides A and B, which both include the amino acid sequence Glu-Glu-Glu, is preferred.

Such oligopeptides A and B different from one another correspond to one another in that they carry three successive Glu amino acids, but have differences in the amino acids bonded before or after. Different peptides which match in part to an extent greater than in the above-mentioned three amino acids are preferred.

Hair treatment agents that are more preferred are thus characterized in that at least two different oligopeptides A and B which both include the amino acid sequence SEQ. ID No.: 2 Glu-Glu-Glu-Ile are included in the hair treatment agent.

Hair treatment agents which include at least two different oligopeptides A and B which both include the amino acid sequence SEQ. ID No.: 1 Tyr-Glu-Glu-Glu are also preferred.

Hair treatment agents that are even more preferred are characterized in that they include at least two different oligopeptides A and B which both include the amino acid sequence SEQ. ID No.: 8 Glu-Glu-Glu-Ile-Arg.

Hair treatment agents that are also even more preferred are characterized in that the hair treatment agent includes at least two different oligopeptides A and B which both include the amino acid sequence SEQ. ID No.: 3 Tyr-Glu-Glu-Glu-Ile.

Hair treatment agents that are preferred in accordance with the invention are therefore characterized in that the oligopeptide includes at least one amino acid sequence SEQ. ID No.: 3 Tyr-Glu-Glu-Glu-Ile

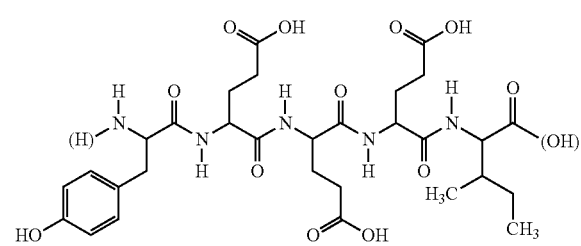

wherein the amino group can be free or protonated and the carboxyl group can be free or deprotonated.

Hair treatment agents that are very particularly preferred are characterized in that the hair treatment agent includes at least two different oligopeptides A and B which both include the amino acid sequence SEQ. ID No.: 8 Glu-Glu-Glu-Ile-Arg.

Hair treatment agents that are also very particularly preferred are characterized in that the hair treatment agent includes at least two different oligopeptides A and B which both include the amino acid sequence SEQ. ID No.: 4 Tyr-Glu-Glu-Glu-Ile-Arg.

There is preferably an even greater structural conformity in the oligopeptides. Hair treatment agents that include at least two different oligopeptides A and B which both include the amino acid sequence SEQ. ID No.: 9 Glu-Glu-Glu-Ile-Arg-Val are thus further preferred embodiments of the present invention.

Embodiments that are also preferred are hair treatment agents that include at least two different oligopeptides A and B which both include the amino acid sequence SEQ. ID No.: 5 Tyr-Glu-Glu-Glu-Ile-Arg-Val.

Hair treatment agents according to the invention that are even more preferred are characterized in that they include at least two different oligopeptides A and B which both include the amino acid sequence SEQ. ID No.: 10 Glu-Glu-Glu-Ile-Arg-Val-Leu.

Hair treatment agents according to the invention that are also even more preferred are characterized in that they include at least two different oligopeptides A and B which both include the amino acid sequence SEQ. ID No.: 6 Tyr-Glu-Glu-Glu-Ile-Arg-Val-Leu.

Hair treatment agents that are preferred in accordance with the invention are therefore characterized in that the oligopeptide includes at least one amino acid sequence SEQ. ID No.: 6 Tyr-Glu-Glu-Glu-Ile-Arg-Val-Leu

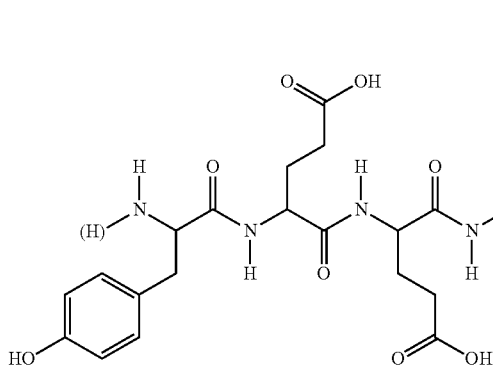
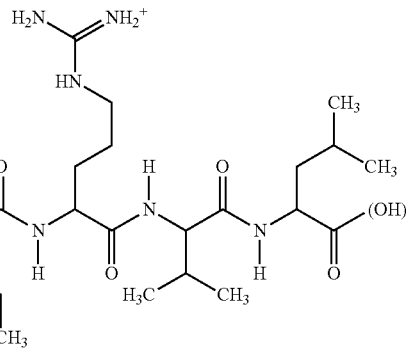

wherein the amino groups can be free or protonated and the carboxyl groups can be free or deprotonated.

Hair treatment agents according to the invention that are particularly preferred are characterized in that they include at least two different oligopeptides A and B, wherein the oligopeptide A includes the amino acid sequence SEQ. ID No.: 7 Leu-Tyr-Glu-Glu-Glu-Ile-Arg-Val-Leu In very particularly preferred hair treatment agents of this last embodiment, these agents include, relative to the weight of the agent, 0.00001 to 1% by weight oligopeptide A and 0.00001 to 1% by weight oligopeptide B.

In hair treatment agents of this last embodiment that are more preferred, these agents include, relative to the weight

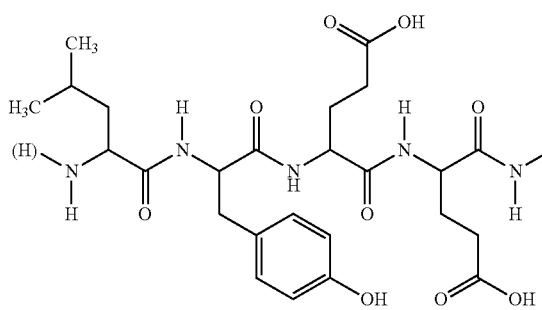
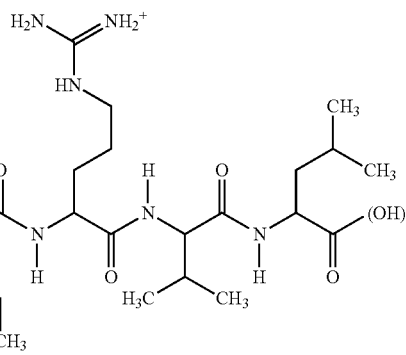

wherein the amino groups can be free or protonated and the carboxyl groups can be free or deprotonated and the oligopeptide B includes the amino acid sequence SEQ. ID No.: 6 Tyr-Glu-Glu-Glu-Ile-Arg-Val-Leu of the agent, 0.00005 to 0.1% by weight oligopeptide A and 0.00005 to 0.1% by weight oligopeptide B.

In hair treatment agents of this last embodiment that are even more preferred, these agents include, relative to the

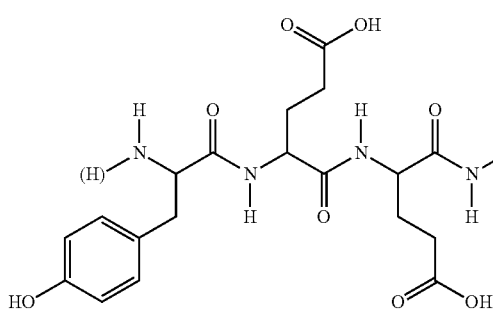

wherein the amino groups can be free or protonated and the carboxyl groups can be free or deprotonated.

weight of the agent, 0.0001 to 0.01% by weight oligopeptide A and 0.0001 to 0.001% by weight oligopeptide B.

The oligopeptides used within the scope of the present invention which meet the above-mentioned requirements can be obtained advantageously from keratinic materials. It is preferred in accordance with the invention for these oligopeptides to be used in high proportions in relation to the total keratinic peptide content of the agents.

It is very particularly preferred that the highest proportion possible of all keratinic peptides included in the agent according to the invention satisfies the above-mentioned conditions.

Preferred hair treatment agents according to the invention are characterized in that at least at least 0.1% by weight, preferably at least 0.5% by weight, particularly preferably at least 1% by weight, more preferably at least 2.5% by weight, even more preferably at least 5% by weight, and in particular at least 10% by weight of all keratinic peptides included in the agent include the amino acid sequence Glu-Glu-Glu.

Hair treatment agents according to the invention that are more preferred are characterized in that at least 0.1% by weight, preferably at least 0.5% by weight, particularly preferably at least 1% by weight, more preferably at least 2.5% by weight, even more preferably at least 5% by weight, and in particular at least 10% by weight of all keratinic peptides included in the agent include the amino acid sequence SEQ. ID No.: 2 Glu-Glu-Glu-Ile.

Hair treatment agents according to the invention that are even more preferred are characterized in that at least 0.1% by weight, preferably at least 0.5% by weight, particularly preferably at least 1% by weight, more preferably at least 2.5% by weight, even more preferably at least 5% by weight, and in particular at least 10% by weight of all keratinic peptides included in the agent include the amino acid sequence SEQ. ID No.: 1 Tyr-Glu-Glu-Glu.

Hair treatment agents according to the invention that are particularly preferred are characterized in that at least 0.1% by weight, preferably at least 0.5% by weight, particularly preferably at least 1% by weight, more preferably at least 2.5% by weight, even more preferably at least 5% by weight, and in particular at least 10% by weight of all keratinic peptides included in the agent include the amino acid sequence SEQ. ID No.: 3 Tyr-Glu-Glu-Glu-Ile.

Hair treatment agents according to the invention that are very particularly preferred are characterized in that at least 0.1% by weight, preferably at least 0.5% by weight, particularly preferably at least 1% by weight, more preferably at least 2.5% by weight, even more preferably at least 5% by weight, and in particular at least 10% by weight of all keratinic peptides included in the agent include the amino acid sequence SEQ. ID No.: 4 Tyr-Glu-Glu-Glu-Ile-Arg.

Hair treatment agents according to the invention that are even more preferred are characterized in that at least 0.1% by weight, preferably at least 0.5% by weight, particularly preferably at least 1% by weight, more preferably at least 2.5% by weight, even more preferably at least 5% by weight, and in particular at least 10% by weight of all keratinic peptides included in the agent include the amino acid sequence SEQ. ID No.: 5 Tyr-Glu-Glu-Glu-Ile-Arg-Val.

Hair treatment agents according to the invention that are preferred in particular are characterized in that at least 0.1% by weight, preferably at least 0.5% by weight, particularly preferably at least 1% by weight, more preferably at least 2.5% by weight, even more preferably at least 5% by weight, and in particular at least 10% by weight of all keratinic peptides included in the agent include the amino acid sequence SEQ. ID No.: 6 Tyr-Glu-Glu-Glu-Ile-Arg-Val-Leu.

The above-mentioned conditions relate to the total content in the agents according to the invention of peptides origi-nating from keratinic materials. In addition to the oligopeptide keratinic origin, further peptides and/or protein hydrolyzates can of course be used, for example from other native sources. By way of example, the additional use of wheat protein hydrolyzates is preferred.

Vitamins are preferably understood to mean the following vitamins, provitamins and vitamin precursors and derivatives thereof:

Vitamin A: the group of substances referred to as vitamin A includes retinol (Vitamin $A_1$) and 3,4-didehydroretinol (Vitamin $A_2$). β-carotin is the provitamin of retinol. Examples of suitable vitamin A components include vitamin A acid and esters thereof, vitamin A aldehyde, and vitamin A alcohol as well as esters thereof, such as the palmitate and acetate.

Vitamin B: the vitamin B group or the vitamin B complex includes, inter alia: vitamin $B_1$ (thiamin); vitamin $B_2$ (riboflavin); vitamin $B_3$, including the compounds of nicotinic acid and nicotinic acid amide (niacinamide); vitamin $B_5$ (pantothenic acid and panthenol), in the context of this group, panthenol is preferably used, useable derivatives of panthenol are especially the esters and ethers of panthenol, pantolactone, and also cationically derivatized panthenols, specific representatives are, for example, panthenol triacetate, panthenol monoethyl ether and monoacetate thereof, as well as cationic panthenol derivatives; vitamin $B_6$ (pyridoxine and also pyridoxamine and pyridoxal).

Vitamin C (ascorbic acid): the use in the form of the palmitic acid ester, the glucosides, or phosphates can be preferred. The use in combination with tocopherols can also be preferred.

Vitamin E: (tocopherols, in particular α-tocopherol).

Vitamin F: the term "vitamin F" is usually understood to mean essential fatty acids, in particular linoleic acid, linolenic acid and arachidonic acid.

Vitamin H: The compound (3aS,4S, 6aR)-2-oxohexahydrothienol[3,4-d]-imidazol-4-valeric acid denotes vitamin H, for which the common name, biotin, has become accepted.

Vitamins, provitamins and vitamin precursors from the groups A, B, E and H are particularly preferred. Nicotinic acid amide, biotin, pantolactone and/or panthenol are preferred in particular. The weight share of the vitamin(s), vitamin derivative(s), and/or the vitamin precursor(s) in the total weight of the hair treatment agent is preferably 0.001 to 2% by weight, particularly preferably 0.005 to 1% by weight, and in particular 0.01 to 0.5% by weight.

Suitable plant extracts are understood to be extracts which can be produced from all parts of a plant. These extracts are usually produced by extraction of the entire plant. However, in individual cases it may also be preferred to produce the extracts exclusively from flowers and/or leaves of the plant. In particular, the extracts from green tea, oak bark, stinging nettle, *hamamelis*, hops, henna, camomile, burdock root, field horsetail, hawthorn, linden flowers, lychee, almonds, aloe vera, spruce needles, horse chestnut, sandal wood, juniper, coconut, mango, apricot, lime, wheat, kiwi, melon, orange, grapefruit, sage, rosemary, birch, malva, lady's smock, broad-leaved thyme, common yarrow, thyme, lemon balm, rest-harrow, coltsfoot, marshmallow, ginseng, ginger root, *echinacea purpurea*, olive, *boerhavia diffusa* root, fennel and celery are suitable.

Extracts from green tea, stinging nettle, *hamamelis*, chamomile, aloe vera, *ginseng, echinacea purpurea*, olive and/or *boerhavia* diffuse root are particularly preferred for use in the compositions according to the invention.

Water, alcohols, and mixtures thereof can be used as extracting agents for producing the specified plant extracts. Here, lower alcohols such as ethanol and isopropanol, but in particular polyvalent alcohols such as ethylene glycol and propylene glycol, both as sole extracting agent and mixed with water, are preferred alcohols. Plant extracts based on water/propylene glycol in a ratio of from 1:10 to 10:1 have proven to be particularly suitable.

The plant extracts can be used both in pure and diluted form. If used in diluted form, they usually include approximately 2 to 80% by weight of active substance and, as solvent, the extracting agent or extracting agent mixture used for their recovery.

The plant extracts can be used in the hair treatment agents according to the invention (in relation to the total weight of the agents) preferably in an amount of from 0.01 to 10% by weight, more preferably from 0.05 to 7.5% by weight, and in particular from 0.1 to 5% by weight.

Glycerol can be added to the hair cleansing and nourishing agents separately in an amount of up to 10% by weight (in relation to the total weight of the agent). However, it can also be part of the aforementioned aqueous-alcoholic carrier.

It has been found that the hair treatment agents according to the invention are also suitable for use as an anti-dandruff preparation.

The total weight of anti-dandruff agents in the total weight of the hair treatment agent can be preferably 0.01 to 10% by weight, more preferably 0.025 to 7.5% by weight, particularly preferably 0.05 to 5% by weight, and in particular 0.075 to 3% by weight.

Suitable anti-dandruff active substances can be selected from piroctone olamines, climbazole, zinc pyrithione, ketoconazoles, salicylic acid, sulfur, selenium sulfide, tea preparations, undecenoic acid derivatives, burdock extracts, poplar extracts, stinging nettle extracts, walnut shell extracts, birch extracts, willow bark extracts, rosemary extracts and/or *arnica* extracts. Climbazole, zinc pyrithione, and piroctone olamines are preferred.

Further active substances, auxiliaries and additives that can be included with preference in the hair treatment agents according to the invention are, for example: humectants; fragrances; UV filters; thickening agents such as gelatins or plant gums, for example agar-agar, guar gum, alginates, xanthan gum, gum arabic, karaya gum, locust bean flour, linseed gums, dextrans, cellulose derivatives, for example methyl cellulose, hydroxyalkyl cellulose and carboxymethyl cellulose, starch fractions and derivatives, such as amylose, amylopectin and dextrins, clays and sheet silicates, such as bentonite or fully synthetic hydrocolloids such as polyvinyl alcohol, the Ca, Mg or Zn soaps; structurants, such as maleic acid and lactic acid; dimethyl isosorbide; cyclodextrins; fiber structure-improving active substances, in particular mono-, di- and oligosaccharides, such as glucose, galactose, fructose, fruit sugar, and lactose; dyes for coloring the agent; active substances such as bisabolol and/or allantoin; complexing agents, such as EDTA, NTA, β-alanine diacetic acid and phosphonic acids; ceramides, understood to mean N-acylsphingosine (fatty acid amides of sphingosine) or synthetic analogues such as lipids (what are known as pseudo ceramides); propellants, such as propane-butane mixtures, $N_2O$, dimethylether, $CO_2$ and air; antioxidants; and/or additional viscosity regulators, such as salts (NaCl).

The agents according to the invention are preferably what are known as rinse-off products, i.e., they are rinsed out of the hair again after a certain reaction time. This reaction time is preferably less than an hour, i.e., the consumer preferably does not leave the products in the hair until the next time the hair is washed.

A further subject of the present invention is therefore a method for treating hair, in which an agent according to the invention is applied to dry or wet hair, is left there for a period of 30 to 300 seconds, and is then rinsed out.

The agents according to the invention lead to a significantly increased strengthening of the internal and external hair structure. A further subject of the present invention is therefore the use of agents according to the invention for strengthening the hair structure, in particular the internal hair structure.

The term "structure strengthening" within the sense of the invention is understood to mean a reduction of the damage to keratinic fibers caused as a result of a wide range of influences. Here, the re-establishment of the natural strength plays a key role, for example. Restructured fibers are characterized for example by an improved shine, by an improved feel, and by an easier combability. In addition, they have optimized strength and elasticity. A successful structure strengthening or restructuring can be verified physically as an increase in the melting point compared to damaged fibers.

That stated with regard to the agents according to the invention applies, mutatis mutandis, in respect of preferred embodiments of the method according to the invention and the use according to the invention.

Examples

All values in % by weight

| | Hair treatments | | | | | |
|---|---|---|---|---|---|---|
| | 1-1 | 1-2 | 1-3 | 1-4 | 1-5 | 1-6 |
| Cetearyl alcohol | 7.0 | 7.0 | 7.0 | 7.0 | 7.0 | 7.0 |
| Quaternium-87 | 0.9 | 0.9 | 0.9 | 0.9 | 0.9 | 0.9 |
| Cetrimonium chloride | 3.5 | 3.5 | 3.5 | 3.5 | 3.5 | 3.5 |
| Distearoylethyl hydroxyethylmonium methosulfate | 2.0 | 2.0 | 2.0 | 2.0 | 2.0 | 2.0 |
| Polyquaternium-10 | 0.1 | 0.1 | 0.1 | 0.1 | 0.1 | 0.1 |
| Baobab seed oil | 0.1 | 0.1 | 0.1 | 0.1 | 0.1 | 0.1 |
| Polyquaternium-37 | 0.4 | 0.4 | 0.4 | 0.4 | 0.4 | 0.4 |
| Hydrolyzed keratin | 0.5 | 0.5 | 0.5 | 0.5 | 0.5 | 0.5 |
| Glycol distearate | 1.0 | 1.0 | 1.0 | 1.0 | 1.0 | 1.0 |
| Citric Acid | 1.5 | 1.5 | 1.5 | 1.5 | 1.5 | 1.5 |
| Dimethicone | 1.0 | 1.0 | 1.0 | 1.0 | 1.0 | 1.0 |
| Amodimethicone | 2.0 | 2.0 | 2.0 | 2.0 | 2.0 | 2.0 |
| o-Cymen-5-ol | 0.06 | 0.06 | 0.06 | 0.06 | 0.06 | 0.06 |
| Phenoxyethanol | 0.2 | 0.2 | 0.2 | 0.2 | 0.2 | 0.2 |
| Ethyl lauroyl arginate | — | 0.3 | 0.3 | 0.3 | 0.3 | 0.3 |
| Dimethyloxazolidine | — | 0.05 | 0.06 | 0.07 | 0.08 | 0.1 |
| Ethyl lauroyl arginate | — | 0.4 | 0.3 | 0.2 | 0.1 | 0.05 |
| Glutaraldehyde | — | 0.05 | 0.06 | 0.07 | 0.08 | 0.1 |
| Hexetidine | — | 0.05 | 0.06 | 0.07 | 0.08 | 0.1 |
| Phenoxyisopropanol | — | 0.05 | 0.05 | 0.05 | 0.05 | 0.05 |
| o-phenylphenol | — | 0.2 | 0.1 | 0.2 | 0.1 | 0.1 |
| Propionic acid | — | 0.05 | 0.1 | 0.25 | 0.05 | 0.05 |
| Undecylenic acid | — | 0.1 | 0.2 | 0.1 | 0.2 | 0.1 |
| Dye | 0.2 | 0.2 | 0.2 | 0.2 | 0.2 | 0.2 |
| Fragrance | 0.1 | 0.1 | 0.1 | 0.1 | 0.1 | 0.1 |
| Water | | | to 100 | | | |

| Hair conditioners | 2-1 | 2-2 | 2-3 | 2-4 | 2-5 | 2-6 |
|---|---|---|---|---|---|---|
| Cetearyl alcohol | 5.0 | 5.0 | 5.0 | 5.0 | 5.0 | 5.0 |
| Quaternium-87 | 0.75 | 0.75 | 0.75 | 0.75 | 0.75 | 0.75 |
| Behentrimonium chloride | 1.0 | 1.0 | 1.0 | 1.0 | 1.0 | 1.0 |
| Behenoyl PG trimonium chloride | 1.5 | 1.5 | 1.5 | 1.5 | 1.5 | 1.5 |
| Glycol distearate | 1.0 | 1.0 | 1.0 | 1.0 | 1.0 | 1.0 |
| Polyquaternium-37 | 0.4 | 0.4 | 0.4 | 0.4 | 0.4 | 0.4 |
| Distearoylethyl hydroxyethylmonium methosulfate | 0.3 | 0.3 | 0.3 | 0.3 | 0.3 | 0.3 |
| Amodimethicone/ morpholinomethyl silsesquioxane copolymer | 0.3 | 0.3 | 0.3 | 0.3 | 0.3 | 0.3 |
| Shea butter | 1.5 | 1.5 | 1.5 | 1.5 | 1.5 | 1.5 |
| Lactic acid | 0.1 | 0.1 | 0.1 | 0.1 | 0.1 | 0.1 |
| o-Cymen-5-ol | 0.1 | 0.1 | 0.1 | 0.1 | 0.1 | 0.1 |
| Phenoxyethanol | 0.5 | 0.5 | 0.5 | 0.5 | 0.5 | 0.5 |
| Dimethyloxazolidine | — | 0.05 | 0.06 | 0.07 | 0.08 | 0.1 |
| Glutaraldehyde | — | 0.05 | 0.06 | 0.07 | 0.08 | 0.1 |
| Hexetidine | — | 0.05 | 0.06 | 0.07 | 0.08 | 0.1 |
| Ethyl lauroyl arginate | — | 0.05 | 0.05 | 0.05 | 0.05 | 0.05 |
| Phenoxyisopropanol | — | 1.0 | 0.5 | 0.25 | 0.2 | 0.1 |
| o-phenylphenol | — | 0.2 | 0.1 | 0.2 | 0.1 | 0.1 |
| Propionic acid | — | 0.05 | 0.1 | 0.25 | 0.05 | 0.05 |
| Undecylenic acid | — | 0.1 | 0.2 | 0.1 | 0.2 | 0.1 |
| Dye | 0.2 | 0.2 | 0.2 | 0.2 | 0.2 | 0.2 |
| Fragrance | 0.1 | 0.1 | 0.1 | 0.1 | 0.1 | 0.1 |
| Water | to 100 | | | | | |

What is claimed is:

1. A hair treatment agent, comprising:
0.1 to 20 by weight of the agent of at least one fatty alcohol,
0.1% to 20% by weight of the agent of at least one cationic surfactant, wherein the cationic surfactant is an alkyltrimethyl ammonium chloride,
an aminofunctional silicone of formula (Si-V),

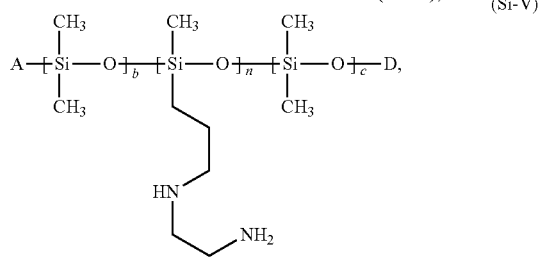

in which:
A is: —OH;
D is —H; and
b, n, and c are integers between 0 and 1000, such that n>0 and (b+c)>0,
0.001% to 0.4% by weight of the agent of o-cymen-5-ol, and
0.01% to 5% by weight of the agent of phenoxyethanol.

2. The hair treatment agent of claim 1, wherein the at least one fatty alcohol is 2% to 8% by weight of the agent.

3. The hair treatment agent of claim 2, wherein the at least one fatty alcohol is a fatty alcohol of formula (II)

$$H_3C-(CH_2)_k-CH_2-OH \quad (II)$$

in which k is an integer from 4 to 28, inclusive.

4. The hair treatment agent of claim 1, wherein the at least one cationic surfactant is 2% to 8% by weight of the agent.

5. The hair treatment agent of claim 1, wherein the at least one cationic surfactant is behenyl trimethyl ammonium chloride.

6. The hair treatment agent of claim 1, wherein the at least one aminofunctional silicone is 1% to 5% by weight of the agent.

7. The hair treatment agent of claim 1, wherein o-cymen-5-ol is 0.05% to 0.1% by weight of the agent.

8. The hair treatment agent of claim 1, wherein phenoxyethanol is 0.1% to 1% by weight of the agent.

9. The hair treatment agent of claim 1, further comprising two different oligopeptides A and B, wherein the oligopeptide A includes the amino acid sequence Leu-Tyr-Glu-Glu-Glu-Ile-Arg-Val-Leu and oligopeptide B includes the amino acid sequence Tyr-Glu-Glu-Glu-Ile-Arg-Val-Leu, wherein oligopeptide A is 0.0001% to 0.001% by weight of the agent, and oligopeptide B is 0.0001% to 0.001% by weight of the agent.

10. A hair treatment agent, comprising:

2% to 8% by weight of the agent of at least one fatty alcohol,

2% to 8% by weight of the agent of at least one cationic surfactant, wherein the at least one cationic surfactant is an alkyltrimethyl ammonium chloride, 1% to 5% by weight of the agent of an aminofunctional silicone, wherein aminofunctional silicone is a silicone(s) of formula (Si-V)

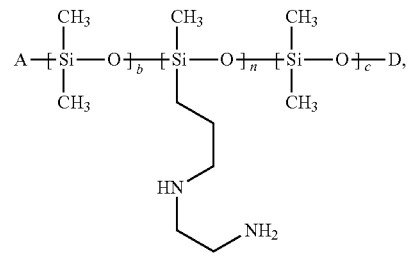

in which:
A is —OH;
D is —H; and
b, n, and c are integers between 0 and 1000, such that n>0 and (b+c)>0, 0.05% to 0.1% by weight of the agent of o-cymen-5-ol, and 0.1% to 1% by weight of the agent of phenoxyethanol.

11. The hair treatment agent of claim 10, wherein the at least one cation surfactant is behenyl trimethyl ammonium chloride and is present from 2% to 8% by weight of the agent.

12. A method of treating hair, comprising:
applying the hair treatment agent of claim 1 to dyed hair.

13. The method of claim 12, further comprising rinsing the agent from the hair after the agent has contacted the hair for 30 to 300 seconds.

* * * * *

SEQUENCE LISTING

<160> NUMBER OF SEQ ID NOS: 10

<210> SEQ ID NO 1
<211> LENGTH: 4
<212> TYPE: PRT
<213> ORGANISM: Triticum aestivum

<400> SEQUENCE: 1

Tyr Glu Glu Glu
1

<210> SEQ ID NO 2
<211> LENGTH: 4
<212> TYPE: PRT
<213> ORGANISM: Triticum aestivum

<400> SEQUENCE: 2

Glu Glu Glu Ile
1

<210> SEQ ID NO 3
<211> LENGTH: 5
<212> TYPE: PRT
<213> ORGANISM: Triticum aestivum

<400> SEQUENCE: 3

Tyr Glu Glu Glu Ile
1               5

<210> SEQ ID NO 4
<211> LENGTH: 6
<212> TYPE: PRT
<213> ORGANISM: Triticum aestivum

<400> SEQUENCE: 4

Tyr Glu Glu Glu Ile Arg
1               5

<210> SEQ ID NO 5
<211> LENGTH: 7
<212> TYPE: PRT
<213> ORGANISM: Triticum aestivum

<400> SEQUENCE: 5

Tyr Glu Glu Glu Ile Arg Val
1               5

```
<210> SEQ ID NO 6
<211> LENGTH: 8
<212> TYPE: PRT
<213> ORGANISM: Triticum aestivum

<400> SEQUENCE: 6

Tyr Glu Glu Glu Ile Arg Val Leu
1               5

<210> SEQ ID NO 7
<211> LENGTH: 9
<212> TYPE: PRT
<213> ORGANISM: Triticum aestivum

<400> SEQUENCE: 7

Leu Tyr Glu Glu Glu Ile Arg Val Leu
1               5

<210> SEQ ID NO 8
<211> LENGTH: 5
<212> TYPE: PRT
<213> ORGANISM: Triticum aestivum

<400> SEQUENCE: 8

Glu Glu Glu Ile Arg
1               5

<210> SEQ ID NO 9
<211> LENGTH: 6
<212> TYPE: PRT
<213> ORGANISM: Triticum aestivum

<400> SEQUENCE: 9

Glu Glu Glu Ile Arg Val
1               5

<210> SEQ ID NO 10
<211> LENGTH: 7
<212> TYPE: PRT
<213> ORGANISM: Triticum aestivum

<400> SEQUENCE: 10

Glu Glu Glu Ile Arg Val Leu
1               5
```